United States Patent [19]

Baget et al.

[11] 4,088,774

[45] May 9, 1978

[54] 2-PHENYL-3-(4-HYDROXYCOUMARIN-3-YL)PHTHALIMIDINE

[75] Inventors: Jean Baget, Sceaux; Jean-Jacques Hucherot, Saint-Maur, both of France

[73] Assignee: Rhone-Poulenc Industries, Paris, France

[21] Appl. No.: 809,277

[22] Filed: Jun. 23, 1977

[30] Foreign Application Priority Data

Jun. 25, 1976 France .................................. 76 19394

[51] Int. Cl.$^2$ ..................... A61K 31/40; C07D 405/04
[52] U.S. Cl. ............................... 424/274; 260/325 PH
[58] Field of Search .................. 260/325 PH; 424/274

[56] References Cited

U.S. PATENT DOCUMENTS

| | | | |
|---|---|---|---|
| 3,466,297 | 9/1969 | Sulkowski et al. | 260/296 B |
| 3,764,693 | 10/1973 | Boschetti et al. | 260/340.5 R |
| 3,849,438 | 11/1974 | Houlihan et al. | 260/325 PH |

FOREIGN PATENT DOCUMENTS 1,070,465   7/1954   France ......................... 260/340.5 R

OTHER PUBLICATIONS

Annalen Der Chemie, vol. 643, pp. 97–106, (1961).

*Primary Examiner*—Alton D. Rollins
*Attorney, Agent, or Firm*—Stevens, Davis, Miller & Mosher

[57] ABSTRACT

3-(4-Hydroxycoumarin-3-yl)-2-phenylisoindolin-1-one possesses useful pharmacological properties, particularly anti-coagulant properties.

2 Claims, No Drawings

2-PHENYL-3-(4-HYDROXYCOUMARIN-3-YL)PHTHALIMIDINE

This invention relates to 3-(4-hydroxycoumarin-3-yl)-2-phenylisoindolin-1-one of the formula:

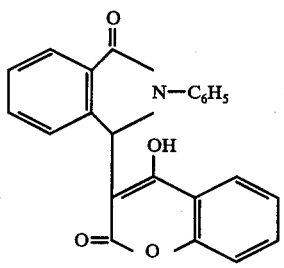

which is therapeutically useful, to a process for its preparation and to pharmaceutical compositions containing it.

According to a feature of the invention, the compound of formula I is prepared by the process which comprises reacting 4-hydroxycoumarin with 3-hydroxy-2-phenylisoindolin-1-one. Generally the reaction is carried out in an organic solvent, such as acetic acid, and in the presence of a strong inorganic acid, for example sulphuric acid, at a temperature of about 20° C.

The product of formula I so obtained can optionally be purified by physical methods such as crystallisation or chromatography.

3-Hydroxy-2-phenylisoindolin-1-one can be prepared in accordance with the method described by A. Dunet, Bull. Soc. Chim., 1045 (1948).

3-(4-Hydroxycoumarin-3-yl)-2-phenylisoindolin-1-one possesses useful pharmacological properties. Administered orally to mice, it shows particularly valuable anticoagulant properties at doses of between 25 and 200 mg/kg animal body weight, and more particularly it favourably alters the Quick time and the cephalin-kaolin time.

The compound of this invention has a low toxicity. Administered orally to mice, it is non-toxic at a dose of 900 mg/kg animal body weight.

The following Example illustrates the preparation of the compound of the invention.

EXAMPLE 1

Sulphuric acid (210 cc) is added dropwise to a suspension of 3-hydroxy-2-phenylisoindolin-1-one (67.5 g) and 4-hydroxycoumarin (97.3 g) in acetic acid (675 cc) whilst maintaining the temperature between 15° and 18° C, and the mixture is stirred for 15 hours at a temperature of about 20° C. The reaction mixture is then run into icewater (3000 cc) and the precipitate is filtered off and washed with water (2500 cc). The filter cake is dried in a stream of air at a temperature of about 20° C. The product obtained is dissolved in dimethylformamide (800 cc) at 90° C. The solution is filtered and acetonitrile (900 cc) is then added. After cooling in an ice-bath for 2 hours, the solid is filtered off and washed with acetonitrile (1000 cc). It is dried under reduced pressure (0.1 mm Hg) for 15 hours at 20° C and then for 4 hours at 55° C and 2 hours at 80° C. 3-(4-Hydroxycoumarin-3-yl)-2-phenylisoindolin-1-one (95 g), melting at 335°–337° C, is thus obtained.

3-Hydroxy-2-phenylisoindolin-1-one can be prepared according to the method of A. Dunet, Bull. Soc., Chim., 1045 (1948).

The present invention also relates to the pharmaceutical compositions which comprise 3-(4-hydroxycoumarin-3-yl)-2-phenylisoindolin-1-one in association with a pharmaceutical carrier or coating. The compositions are preferably employed orally and it is particularly recommended to use solid compositions.

Tablets, pills, powders or granules can be used as solid compositions for oral administration. In these compositions, the compound of the invention is admixed with at least one inert diluent such as sucrose, lactose or starch. These compositions can also contain substances other than inert diluents, for example a lubricant such as magnesium stearate.

The compositions according to the invention are particularly useful for the prophylaxis and treatment of thrombo-embolic illnesses.

In human therapy, the doses depend on the desired effect and on the duration of the treatment. The initial dose is generally between 10 and 300 mg and the maintaining doses are between 5 and 150 mg and depend, on the one hand, on the patient and, on the other hand, on the results obtained in the course of regular monitoring of the prothrombin level and of the overall coagulability of blood.

The following Example illustrates a pharmaceutical composition according to the invention.

EXAMPLE 2

Cuttable tablets containing a dose of 100 mg and having the following composition are prepared in accordance with the usual technique:

3-(4-hydroxycoumarin-3yl)-2-phenylisoindolin-1-one: 100 mg
starch: 100 mg
precipitated silica: 45 mg
magnesium stearate: 5 mg.

We claim:
1. 3-(4-Hydroxycoumarin-3-yl)-2-phenylisoindolin-1-one.
2. A pharmaceutical anticoagulant composition useful in human therapy which comprises an effective anticoagulant amount of 3-(4-hydroxycoumarin-3-yl)-2-phenylisoindolin-1-one as claimed in claim 1 in association with a compatible pharmaceutical carrier.

* * * * *